United States Patent
Beauchamp et al.

(10) Patent No.: US 7,205,297 B2
(45) Date of Patent: Apr. 17, 2007

(54) SUBSTITUTED 5-ALKYNYL PYRIMIDINES HAVING NEUROTROPHIC ACTIVITY

(75) Inventors: Lilia M. Beauchamp, Raleigh, NC (US); Thomas A. Krenitsky, Chapel Hill, NC (US); James L. Kelley, Raleigh, NC (US)

(73) Assignee: Krenitsky Pharmaceuticals, Inc., Durham, NC (US)

( * ) Notice: Subject to any disclaimer, the term of this patent is extended or adjusted under 35 U.S.C. 154(b) by 417 days.

(21) Appl. No.: 10/333,447

(22) PCT Filed: Jul. 20, 2001

(86) PCT No.: PCT/US01/23088

§ 371 (c)(1),
(2), (4) Date: Jun. 27, 2003

(87) PCT Pub. No.: WO02/08205

PCT Pub. Date: Jan. 3, 2002

(65) Prior Publication Data

US 2004/0087789 A1 May 6, 2004

Related U.S. Application Data

(60) Provisional application No. 60/220,348, filed on Jul. 24, 2000.

(51) Int. Cl.
*C07D 239/34* (2006.01)
*A61K 31/505* (2006.01)

(52) U.S. Cl. .............. 514/235.8; 514/252.14; 514/256; 514/275; 544/122; 544/325; 544/326; 544/330; 544/332

(58) Field of Classification Search ......... 544/122, 544/325, 326, 330, 332; 514/235.8, 252.14, 514/256, 275
See application file for complete search history.

(56) References Cited

U.S. PATENT DOCUMENTS

| | | | |
|---|---|---|---|
| 2,691,655 A | 10/1954 | Hitchings et al. | |
| 3,154,551 A | 10/1964 | Hitchings et al. | |
| 3,862,190 A | 1/1975 | Lipinski et al. | |
| 3,947,441 A | 3/1976 | Schweizer et al. | |
| 4,508,560 A | 4/1985 | Brunner et al. | |
| 4,626,272 A | 12/1986 | Brunner et al. | |
| 4,663,334 A | 5/1987 | Carson | |
| 5,075,305 A | 12/1991 | Hobbs et al. | |
| 5,525,604 A | 6/1996 | Lee et al. | |
| 5,719,303 A | 2/1998 | Yoshida et al. | |
| 6,440,965 B1 | 8/2002 | Kelley et al. | |
| 6,583,148 B1 | 6/2003 | Kelley et al. | |

FOREIGN PATENT DOCUMENTS

| | | |
|---|---|---|
| CA | 2045327 A1 | 1/1992 |
| DE | 25 33 710 A1 | 2/1976 |
| DE | 2 829 820 | 2/1979 |
| EP | 0 372 934 A2 | 6/1990 |
| EP | 0 459 819 A2 | 12/1991 |
| EP | 0 508 469 A1 | 10/1992 |
| EP | 0 640 599 A1 | 3/1995 |
| EP | 0 826 674 A1 | 3/1998 |
| FR | 2 358 148 | 2/1978 |
| GB | 2 262 096 A | 6/1993 |
| JP | 08 283246 A | 10/1996 |
| WO | WO 92/18498 A1 | 10/1992 |
| WO | WO 93 08169 A1 | 4/1993 |
| WO | WO 94 14780 A1 | 7/1994 |
| WO | WO 96/31488 A1 | 10/1996 |
| WO | WO 99 02497 A2 | 1/1999 |
| WO | WO 99 19305 A2 | 4/1999 |
| WO | WO 00 61562 A1 | 10/2000 |

OTHER PUBLICATIONS

Ulrich, Chapter 4: Crystallization, Kirk-Othmer Encyclopedia of Chemical Technology, Aug. 2002.*
Vippagunta et al., Cyrstalline Solids, Advanced Drug Delivery Reviews, 48, pp. 3-26, 2001.*
West, Solid Solutions, Solid State Chemistry and its applications, pp. 358 & 365, 1988.*
Aroyan, et al., "Pyrimidine derivatives. X. Synthesis of amino and hydrazino derivatives of 2-(methylthio)-5-(p-alkoxybenzyl)-6-methyl pyrimidines, and a study of their antineoplastic activity", *Chemical Abstracts*, 1969, p. 347, vol. 71, No. 21.
Aroyan, et al., "Pyrimidine derivatives. XLIV. Synthesis and some reactions of 2-phenyl-4-hydroxy-5-(p-alkoxybenzyl)-6-methylpyrimidines", *Chemical Abstracts*, 1976, p. 515, vol. 84, No. 9.
Aroyan, et al., "Pyrimidine derivatives. XXXV. Synthesis of 2, 4-bis(arylamino)- and 2, 4-bis(aryloxy)-5- (p-alkoxybenzyl)-6-methylpyrimidines", *Chemical Abstracts*, 1975, p. 601, vol. 82, No. 23.
Aroyan, et al., "Synthesis and some reactions of 4-hydroxy-5-(p-alkoxybenzyl)-6-methyl-2-mercapto- (and 2-amino- )pyrimidines" *Chemical Abstracts*, 1968, p. 1241, vol. 68, No. 3.
Awaya, et al. "Neurotropic Pyrimidine Heterocycle Compounds. I. The Newly Synthesized Pyrimidine Compounds Promote Neurite Outgrowth of GOTO and Neuro 2a Neuroblastoma Cell Lines, and Potentiate Nerve Growth Factor (NGF)-Induced Neurite Sprouting of PC 12 Cells", *Biol. Pharm. Bull.*, 1993, pp. 248-253, Pharmaceutical Society of Japan, vol. 16(3).

(Continued)

*Primary Examiner*—Deepak Rao
(74) *Attorney, Agent, or Firm*—Alston & Bird LLP

(57) ABSTRACT

The present invention relates to a series of novel substituted 5-alkynyl pyrimidines, pharmaceutical compositions which contain them, methods for their preparation, and their use in therapy, particularly in the treatment of neurodegenerative or other neurological disorders of the central and peripheral nervous systems, including age related cognitive disorders such as senility and Alzheimer's disease, nerve injuries, peripheral neuropathies, and seizure disorders such as epilepsy.

40 Claims, No Drawings

OTHER PUBLICATIONS

Chemical Abstracts, 1997, p. 620, col. 2, vol. 126, No. 7, abstract No. 89387x.

Curd, et al. "74. Synthetic antimalarials. Part VII. 2-Arylamino-4-dialkylaminoalkylaminopyrimidines. Variation of substituents in the 5- and the 6-position" *J. Chem. Soc.*, 1946, pp. 378-384.

E.A. Coats et al., "Correlation Analysis of Pyrimidine Folic Acid Antagonists as Antibacterial Agents .I.", *Euro. J. Med. Chem. —Chemica Therapeutica*, May 1979, pp. 261-270, vol. 14, No. 3, Editions Scientifique Elsevier, Paris.

Falco, et al. "5-Arylthiopyrimidines. I. 2, 4-Diamino Derivatives", *J. Org. Chem..*, 1961, pp. 1143-1146, vol. 26.

Goldberg, A., "No. 218. Préparation de quelques 5-benzyl pyrimidines"*Bulletin De La Societe Chimique France*, 1951, pp. 895-899.

Hull, et al. "70. Synthetic antimalarials. Part III. Some derivatives of mono- and di-alkylpyrimidines", *J. Chem. Soc.*, 1946, pp. 357-362.

Hull, et al. "9. Synthetic antimalarials. Part XI. The effect of variation of substituents in derivatives of mono- and di-alkylpyrimidines" *J. Chem. Soc.*, 1947, pp. 41-52.

Kramer, et al., "Pyrimidine derivatives. XVI. 4-(p-Alkoxyphenyl)-2, 6-dimethyl-4-pyrimidinylaminophosphonic diaziridides", *Chemical Abstracts*, 1970, p. 326, vol. 73, No. 7.

Lehmann, et al., *Neurite Outgrowth of Neurons of Rat Dorsal Root Ganglia Induced By New Neurotrophic Substances With Guanidine Group*, Neuroscience Letters, 1993, pp. 57-60, Elsevier Scientific Publishers Ireland, Ltd. vol. 152.

Ordukhanyan, et al., "Study of the relation between structure and biological activity. II. Antineoplastic activity of pyrimidine derivatives", *Chemical Abstracts*, 1980, p. 25, vol. 92, No. 3.

Roth, et al. "5-Arylthiopyrimidines. II. 2- and 4-Alkylamino and 4-Amino Derivatives", *J. Org. Chem..*, 1961, pp. 2770-2778, vol. 26.

Roth, et al. "5-Benzyl-2,4-diaminopyrimidines as antibacterial agents. I. Synthesis and antibacterial activity in vitro" *J. Med. Pharm. Chem..*, 1962, pp. 1103-1123, vol. 5.

Samano, et al., "An Improved Synthesis of 2-Amino-5-[(4-chlorophenyl)thio]-4-morpholinopyrimidine (BW 394U)—A Potential Antisenility Agent", *J. Heterocyclic Chem.*, Jan.-Feb. 2000, pp. 183-185, vol. 37.

Vaillancourt, et al., "Synthesis and Self-Association of 4-Pyrimidinones", *J. Org. Chem.*, 1998, pp. 9746-9752, vol. 63, No. 26.

* cited by examiner

SUBSTITUTED 5-ALKYNYL PYRIMIDINES HAVING NEUROTROPHIC ACTIVITY

CROSS-REFERENCE TO RELATED APPLICATIONS

This application is a 35 U.S.C. 371 national phase application of International Application No. PCT/US01/23088, filed Jul. 20, 2001, which claims the benefit of U.S. Provisional Application No. 60/220,348, filed Jul. 24, 2000, both of which are incorporated herein by reference in their entirety.

BACKGROUND OF THE INVENTION

The present invention relates to a series of novel substituted 5-alkynyl pyrimidines, to pharmaceutical compositions which contain them, to methods for their preparation and to their use in therapy, particularly in the treatment of neurodegenerative or other neurological disorders of the central and peripheral nervous systems including age related cognitive disorders such as senility and Alzheimer's disease, nerve injuries, peripheral neuropathies, and seizure disorders such as epilepsy.

Dementing disorders such as age-related cognitive disorders, e.g., senility or Alzheimer's disease are medical conditions for which there are currently only limited therapies. Although studies suggest that multiple neurotransmitter systems are involved in senile dementia, a loss of cholinergic neurons and a severe depletion of choline acetyltransferase appear to show the earliest and strongest correlation with functional cognitive impairment [see P. T. Francis et al., Neurochemical Studies of Early-onset Alzheimer's Disease. N. Engl. J. Med., 313, 7 (1985); R. T. Bartus et al., The Cholinergic Hypothesis: A Historical Overview, Current Perspective, and Future Directions. Ann. N. Y. Acad. Sci., 444, 332 (1985); F. Hefti and L. S. Schneider, Nerve Growth Factor and Alzheimer's Disease, Clin. Neuropharmacol., 14, S62 (1991)]. Several groups have attempted to stimulate cholinergic activity by blocking the breakdown of acetylcholine with acetylcholine esterase inhibitors or by introducing muscarinic or nicotinic agonists [see R. T. Bartus et al., The Cholinergic Hypothesis of Geriatric Memory Dysfunction. Science, 217, 408 (1982); J. Varghese et al., Chapter 21. Alzheimer's Disease: Current Therapeutic Approaches. Annu. Rep. Med. Chem., 28, 197 (1993)]. The approved drugs COGNEX and ARICEPT are acetylcholine esterase inhibitors.

Nerve growth factor (NGF) is the best characterized neurotrophic factor that is capable of inducing cell differentiation of neural cells and promoting neurite sprouting. The neurotrophic protein NGF primarily affects cholinergic neurons in the central nervous system and may be necessary for their survival [see F. Hefti and P. A. Lapchak, Pharmacology of Nerve Growth Factor in the Brain. Adv. Pharmacol., 24, 239 (1993)]. NGF is not systemically bioavailable, but if it is injected or infused directly into brain, it prevents neuronal cell loss and restores cognitive function in aged or lesioned rats or monkeys [see W. Fischer et al., NGF Improves Spatial Memory in Aged Rodents as a Function of Age. J. Neurosci., 11, 1889 (1991)]. NGF effects ultimately result in the stimulation of choline acetyltransferase, the enzyme for biosynthesis of acetylcholine and the promotion of neurite growth. Consequently, small molecules that produce neurotrophic or "nerve growth factor-like" (NGF-like) properties in mammalian cell cultures have potential for use in the treatment of dementing disorders such as age-related senility or Alzheimer's disease and other neurodegenerative conditions such as peripheral neuropathies, Parkinson's, stroke damage, transient ischemic attacks, trauma-head injuries or other nerve injuries.

Since pancreatic cells producing insulin synthesize, secrete and are stimulated by nerve growth factor, another potential use of the compounds of the present invention is in the treatment of diabetes. [See T. Rosenbaum et al., Pancreatic B Cells Synthesize and Secrete Nerve Growth Factor, Proc. Natl. Acad. Sci. USA, 95, 7784 (1998)].

There are several reports of small molecules that exhibit various aspects of NGF-like activity. Isaxonine [2-(isopropylamino)pyrimidine] was developed as a neurotrophic pharmaceutical but the clinical application was withdrawn, possibly due to toxicological effects [see S. Lehmann et al., Neurite Outgrowth of Neurons of Rat Dorsal Root Ganglia Induced by New Neurotrophic Substances with Guanidine Group. Neurosci. Lett., 152, 57 (1993)]. Several 2-(piperazino)pyrimidine derivatives were reported to possess NGF-like activity and are being studied further for use in treating CNS degenerative diseases [see A. Awaya et al., Neurotrophic Pyrimidine Heterocyclic Compounds. Biol. Pharm. Bull., 16, 248 (1993)]. AIT-082 (4[[3-(1,6-dihydro-6-oxo-9-purin-9-yl)-1-oxopropyl]amino]benzoic acid) is reported to enhance NGF action in cultured PC-12 cells and to restore age-induced working memory deficits in mice [see P. J. Middlemiss et. al., AIT-082, A Unique Purine Derivative, Enhances Nerve Growth Factor Mediated Neurite Outgrowth from PC-12 cells. Neuroscience Let., 199, 131 (1995)]. The compound SR57746A is reported to have nerve growth factor potentiating activity and is in clinical trials [see Fournier J, et al. Protective Effects of SR57746A in Central and Peripheral Models of Neurodegenerative Disorders in Rodents and Primates. Neuroscience, 55(3), 629–41, August 1993; U.S. Pat. Nos. 5,270,320 and 5,462, 945]. The compound BW 394U, 2-amino-5-(4-chlorophenyl)thio-4-morpholinopyrimidine, is described as a potential antisenility agent [see Samano et. al., J. Heterocyclic Chem., 37, 183 (2000)]. In addition, WO98/12190, WO99/19305, WO00/59893, WO00/61562, EP0372934, EP0459819 and U.S. Pat. No. 5,075,305 disclose substituted pyrimidines having NGF-like activity and their possible use in treating CNS degenerative diseases like Alzheimer's disease as well as peripheral neuropathies and other disorders of the central and peripheral nervous system. WO94/14780 discloses certain structurally similar pyrimidine derivatives as neuronal nitric oxide synthase inhibitors.

SUMMARY OF THE INVENTION

We have now discovered a novel series of substituted 5-alkynyl pyrimidines that demonstrate NGF-like activity and/or enhancement of NGF activity in PC12 cells. The compounds stimulated both neurite outgrowth and choline acetyltransferase activity in in vitro experiments. Such activities are predictive for causing increased choline acetyltransferase activity in rat striatum and improving cognitative performance in animal models of age-induced working memory deficits by potentiating the activity of endogenous NGF in the brain. [see P. J. Middlemiss, A. J. Glasky, M. P. Rathbone, E. Werstuik, S. Hindley and J. Gysbers, AIT-082, A Unique Purine Derivative, Enhances Nerve Growth Factor Mediated Neurite Outgrowth from PC-12 cells. Neuroscience Let., 199, 131 (1995); A. J. Glasky, C. L. Melchior, B. Pirzadeh, N. Heydari and R. F. Ritzmannn, Effect of AIT-082, a Purine Analog, on Working Memory in Normal and Aged Mice. Pharmacol. Biochem. Behav., 47, 325

(1994); R. Morris, Developments of a Water-maze Procedure for Studying Spatial Learning in the Rat. J. Neurosci. Methods, 11, 47 (1984)].

DETAILED DESCRIPTION OF THE INVENTION

According to the present invention, there are provided novel compounds of Formula I:

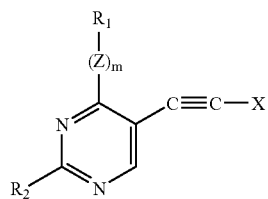

Formula I wherein
Z is O, NH or S, and m is 0 or 1;
$R_1$ is $(C2–6alkyl)_a(C3–10cycloalkyl, C2–9heterocycloalkyl, C5–10aryl, or C4–9heteroaryl)_b(C1–6alkyl)_c$, wherein a, b and c are independently 0 or 1, provided that at least one of a, b and c is 1 and if b is 0, then c is also 0, and wherein the hetero groups include an N, O or S atom and the C and N atoms of $R_1$ may optionally be substituted with one or more substituents selected from the group consisting of:
OH;
halogen:
thio;
oxo;
thioxo;
carboxy;
carboxamide;
C1–7alkylcarbonyl;
C1–7alkylcarbonyloxy
C1–7alkylthiocarbonyl;
C1–8alkyloxy;
hydroxyC2–8alkyloxy;
di-C1–8alkylphosphate ester
C1–8alkylthio;
hydroxyC2–8alkylthio;
C1–8alkylsulfinyl;
C1–8alkylsulfonyl;
C1–5alkyloxyC1–5alkyl;
C1–5alkylthioC1–5alkyl;
C1–5alkylsulfinylC1–5alkyl; and
C1–5alkylsulfonylC1–5alkyl;
$R_2$ is selected from the group consisting of H, $NH_2$ and NH—CO—$R_3$, where $R_3$ is H or C1–12 alkyl;
X is C6–10aryl optionally substituted with one or more substituents (y) selected from the group consisting of:
OH;
$NO_2$
$NH_2$
NH—CO—$R_4$ where $R_4$ is H, C1–12alkyl, aryl or (C1–6alkyl)aryl
halogen;
C1–6alkyl;
hydroxyC1–6alkyl;
oxoC2–7alkyl;
C2–7alkenyl;
C2–7alkynyl;
C1–6alkoxy;
$CF_3$;
$CF_3$C1–6alkyl;
$OCF_3$; and
$CF_3$C1–6alkoxy;

and pharmaceutically acceptable esters, amides, salts or solvates thereof.

By "alkyl" is meant straight or branched chain alkyl. By "heterocycloalkyl" is meant a saturated ring containing 1 to 4 heteroatoms selected from the group consisting of N, O and S. By "aryl" is meant an aromatic ring such as phenyl or naphthyl. By "heteroaryl" is meant an aromatic ring containing 1 to 4 heteroatoms selected from the group consisting of N, O and S. By "halogen" is meant F, Cl, Br or I.

The present invention includes all enantiomeric and diastereomeric forms of the compounds of Formula I either individually or admixed in any proportion.

The present invention further includes prodrugs and active metabolites of the compounds of Formula I. A prodrug includes any compound which, when administered to a mammal, is converted in whole or in part to a compound of Formula I. As is well known in the pharmaceutical arts, a specific drug compound may be utilized in its active form, or in the form of a "prodrug" which is converted to the active form (or to an active metabolite) of the compound when administered to the patient. In the present invention, esters or amides of the compounds of Formula I which are hydrolyzed in the body to form the compounds of Formula I are examples of prodrugs of such compounds. An active metabolite is a physiologically active compound which results from the metabolism of a compound of Formula I, or a prodrug thereof, when such compound or prodrug is administered to a mammal. It is well know that drugs are metabolized by the body into a variety of derivative compounds, one or more of which may be responsible in whole or in part for the recognized activity of the drug. Such metabolites of the drug constitute an inherent part of the underlying drugs of the present invention, but must be identified individually for each compound by blood analysis of the patient. Such identification is well within the skill of the art and is routinely practiced as a part of the clinical evaluation and regulatory approval process for commercial drug products. Accordingly, while specific metabolites cannot be identified herein for all the compounds encompassed by the present invention, the identification of metabolites for any given compound is merely a routine undertaking once that compound has been selected for administration to a mammal. Prodrugs and active metabolites of the compounds of the present invention, therefore, are an inherent part of the invention and intended to be included within the scope thereof.

Preferred compounds of Formula I are those wherein X is phenyl which is unsubstituted or substituted at the 4-position. Particularly preferred are those compounds wherein X is phenyl substituted with 4-chloro, 2,4 dichloro, 4-bromo, 2-fluoro-4-chloro, 2-chloro-4-fluoro, 2-methyl-4-chloro, 4-methyl, 4-ethyl or 4-acetamido. Also preferred are those compounds wherein $R_1$ is an oxy or hydroxy substituted phenyl, phenylethyl, cyclohexyl, alkyl or alkoxyalkyl. Particularly preferred are those compounds where $(Z)_m$-$R_1$ is 4-oxocyclohexylamino, trans-4-hydroxy-cyclohexylamino, cis-4-hydroxycyclohexylamino, 4-hydroxyanilino, 4-methoxyanilino, 3,4-dimethoxyanilino, 4-hydroxypiperdino, 2-hydroxyethylamino or 2-(2-hydroxyethoxy)ethyl-amino. Yet further preferred compounds of Formula I are those where $R_2$ is $NH_2$ or formamido. The compounds of Formula I above and their pharmaceutically acceptable salts or solvates are sometimes hereinafter referred to as "compounds of the present invention".

Preferred compounds of Formula I are more particularly defined according to the following Formulas IA–IC:

Formula IA

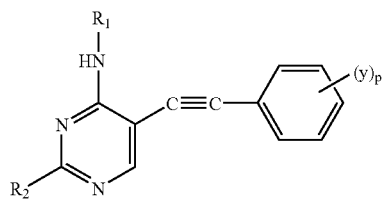

wherein p is 0, 1 or 2, and each y (which may be the same or different), $R_1$ and $R_2$ are as hereinbefore defined;

Formula IB

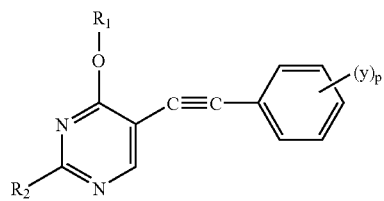

wherein p is 0, 1 or 2, and each y (which may be the same or different), $R_1$ and $R_2$ are as hereinbefore defined;

Formula IC

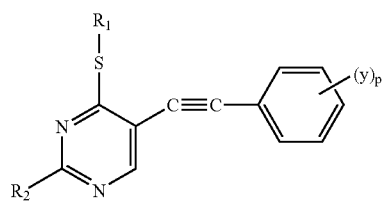

wherein p is 0, 1 or 2, and each y (which may be the same or different), $R_1$ and $R_2$ are as hereinbefore defined.

Representative compounds of the present invention are:
2-Amino-5-(4-chlorophenylethynyl)-4-(4-acetylpiperazino)pyrimidine
4-(trans-4-Hydroxycyclohexylamino)-5-phenylethynylpyrimidine
4-[2-(2-Hydroxyethoxy)ethylamino]-5-phenylethynylpyrimidine
5-(4-Chlorophenylethynyl)-4-[2-(2-hydroxyethoxy)ethylamino]pyrimidine
2-Amino-5-(4-chlorophenylethynyl)4-[2-(2-hydroxyethoxy)ethylamino]pyrimidine
4-[4-(2-Hydroxyethyl)piperazino]-5-phenylethynylpyrimidine
2-Amino-4-[4-(2-hydroxyethyl)piperazino]-5-phenylethynylpyrimidine
2-Amino-5-(4-chlorophenylethynyl)-4-[4-(2-hydroxyethyl)piperazino]pyrimidine
4-(4-Hydroxypiperidino)-5-phenylethynylpyrimidine
5-(4-Chlorophenylethynyl)-4-(4-hydroxypiperidino)pyrimidine
2-Amino-4-(4-hydroxypiperidino)-5-phenylethynylpyrimidine
2-Amino-5-(4-chlorophenylethynyl)-4-(4-hydroxypiperidino)pyrimidine
4-(2-Hydroxyethylamino)-5-phenylethynylpyrimidine
2-Amino-4-(2-hydroxyethylamino)-5-phenylethynylpyrimidine
2-Amino-4-(4-hydroxyanilino)-5-phenylethynylpyrimidine
2-Amino-4-(4-trans-hydroxycyclohexylamino)-5-(4-n-pentylphenylethynyl) pyrimidine
2-Acetamido-4-(4-trans-acetoxycyclohexylamino)-5-(4-chlorophenylethynyl) pyrimidine
2-Amino-5-(4-t-butylphenylethynyl)-4-(4-trans-hydroxycyclohexylamino) pyrimidine
2-Amino-5-(4-chlorophenylethynyl)-4-(4-hydroxyphenylethylamino)pyrimidine
2-Amino-4-(4-hydroxyanilino)-5-(4-methoxyphenylethynyl)pyrimidine
2-Amino-5-(4-propylphenylethynyl)-4-(4-trans-hydroxycyclohexylamino) pyrimidine
2-Amino-4-(4-hydroxy-2-methylanilino)-5-(4-chlorophenylethynyl)pyrimidine
2-Amino-5-(4-chlorophenylethynyl)-4-(4-hydroxyanilino) pyrimidine
2-Amino-5-(4-chlorophenylethynyl)-4-(4-oxocyclohexyloxo)pyrimidine
2-amino-5-(4-chlorophenylethynyl)-4-[2-(2-hydroxyethoxy)ethoxy]pyrimidine
2-amino-5-(4-chlorophenylethynyl)-4-(4-hydroxyphenoxy) pyrimidine
2-amino-5-(4-chlorophenylethynyl)-4-(4-hydroxyphenylthio)pyrimidine, and
5-(4-chlorophenylethynyl)-2-formamido-4-(4-hydroxyphenylthio)pyrimidine and the pharmaceutically acceptable esters, amides, salts or solvates thereof.

Preferred compounds of the present invention are:
4-(4-Hydroxyanilino)-5-phenylethynylpyrimidine
5-(4-Chlorophenylethynyl)-4-(4-hydroxyanilino)pyrimidine
2-Amino-4-[2-(2-hydroxyethoxy)ethylamino]-5-(4-methylphenylethynyl)pyrimidine
2-Amino-4-(trans-hydroxycyclohexylamino)-5-(4-methylphenylethynyl)pyrimidine
5-(4-Chlorophenylethynyl)-2-formamido-4-(4-trans-hydroxycyclohexylamino) pyrimidine
2-Amino-5-(3,4-dichlorophenylethynyl)-4-(4-trans-hydroxycyclohexylamino) pyrimidine
2-Amino-5-(4-chlorophenylethynyl)-4-(4-oxocyclohexylamino)pyrimidine
2-Amino-5-(2-chlorophenylethynyl)-4-(4-trans-hydroxycyclohexylamino) pyrimidine
2-Amino-5-(4-bromophenylethynyl)-4-(4-trans-hydroxycyclohexylamino) pyrimidine
2-Amino-5-(4-chlorophenylethynyl)-4-(4-trans-hydroxycyclohexylamino) pyrimidine-O-dimethylphosphate ester
2-Amino-5-(4-chlorophenylethynyl)-4-(3,4-dimethoxyanilino)pyrimidine
5-(4-Acetamidophenylethynyl)-2-amino-4-(4-trans-hydroxycyclohexylamino) pyrimidine and the pharmaceutically acceptable esters, amides, salts or solvates thereof.

Particularly preferred compounds of the present invention are:

5-(4-Chlorophenylethynyl)-4-(trans-4-hydroxycyclohexylamino)pyrimidine
2-Amino-5-(4-chlorophenylethynyl)-4-(4-hydroxyanilino)pyrimidine
2-Amino-4-(trans-4-hydroxycyclohexylamino)-5-phenylethynylpyrimidine
2-Amino-5-(4-chlorophenylethynyl)-4-(trans-4-hydroxycyclohexylamino) pyrimidine
2-Amino-5-(4-chlorophenylethynyl)-4-(cis-4-hydroxycyclohexylamino)pyrimidine
2-Amino-4-[2-(2-hydroxyethoxy)ethylamino]-5-phenylethynylpyrimidine
2-Amino-5-(4-chlorophenylethynyl)-4-(2-hydroxyethylamino)pyrimidine
2-Amino-5-(4-ethylphenylethynyl)-4-(4-trans-hydroxycyclohexylamino)pyrimidine and the pharmaceutically acceptable esters, amides, salts or solvates thereof.

In one aspect of the invention, compounds of the present invention are provided for use in medical therapy, particularly for the treatment of neurodegenerative or neurological disorders of the central or peripheral nervous systems.

Examples of nervous system disorders which may be treated in accordance with the invention include dementing disorders such as age-related senility, senile dementia or Age Related Mental Impairment (ARMI), cerebal ataxia, Parkinson's disease, Alzheimer's disease, peripheral neuropathy, cognitive disorders secondary to stroke or trauma and attention-deficit hyperactivity disorder. In addition, nerve injuries, for example, spinal cord injuries, that require neuroregeneration may also be treated in accordance with the invention.

In another aspect of the invention, compounds of the present invention are provided for use in the treatment of seizure disorders such as epilepsy.

In a further aspect of the invention, compounds of the present invention are provided for use in the treatment of diabetes.

In a further aspect of the present invention there is included:
a) A method for the treatment of neurodegenerative or neurological disorders of the central or peripheral nervous systems which comprises treating the subject, e.g., a mammal, such as a human, with a therapeutically effective amount of a compound of the present invention;
b) A method for the treatment of seizure disorders which comprises treating the subject, e.g., a mammal such as a human, with a therapeutically effective amount of a compound of the present invention;
c) A method for the treatment of diabetes which comprises treating the subject, e.g., a mammal such as a human, with a therapeutically effective amount of a compound of the present invention; and
d) The use of a compound of the present invention in the manufacture of a medicament for the treatment of any of the above mentioned disorders.

In addition, since the compounds of the present invention have been shown to enhance differentiation signals but not mitotic signals to cells in culture, the compounds can be used in clinical situations where enhancement of differentiation signals would be of benefit to the patient, as, for example, in the study of tumors derived from stem cells where the differentiation signals are overpowered by the mitotic signals.

Examples of pharmaceutically acceptable salts of the compounds of the present invention include acid addition salts. However, salts of non-pharmaceutically acceptable acids may be of utility in the preparation and purification of the compounds of the present invention. Preferred salts include those formed from hydrochloric, hydrobromic, sulfuric, phosphoric, citric, tartaric, lactic, pyruvic, acetic, succinic, fumaric, maleic, oxaloacetic, methanesulfonic, ethanesulfonic, p-toluenesulfonic, benzenesulfonic and isethionic acids.

Examples of pharmaceutically acceptable esters of the compounds of the present invention include straight chain or branched aliphatic esters such as the formyl, acetyl, n-butyl, isobutyl and t-butyl esters, aromatic or substituted aromatic esters such as the benzoyl, naphthoyl and p-chlorobenzoyl esters, alkylaryl esters such as the phenylacetyl, naphthylacetyl and benzyl esters, and amino acid esters such as the L-valyl, L-isoleucyl and L-phenylalanyl esters. Many of these esters are hydrolysed to the compounds of Formula I upon administration to mammals and accordingly constitute prodrugs of the compounds of Formula I.

The compounds of the present invention and pharmaceutically acceptable esters, amides, salts or solvates thereof may be employed in combination with other therapeutic agents for the treatment of the above disorders. Examples of such further therapeutic agents include COGNEX, ARICEPT and other agents (e.g., acetylcholine esterase inhibitors, muscarinic or nicotinic receptor agonists, MAO inhibitors) that are effective for the treatment of neurodegenerative or neurological disorders of the central or peripheral nervous systems. The component compounds of such combination therapy may be administered simultaneously in either separate or combined formulations, or at different times, e.g., sequentially such that a combined effect is achieved.

While it is possible for compounds of the present invention to be administered as the raw chemical, it is preferable to present them as a pharmaceutical formulation. The formulations of the present invention comprise a compound of Formula I, as above defined, or a pharmaceutically acceptable ester, amide, salt or solvate thereof, together with one or more pharmaceutically acceptable carriers therefor and optionally other therapeutic ingredients. The carrier(s) must be acceptable in the sense of being compatible with the other ingredients of the formulation and not deleterious to the recipient thereof.

The formulations include those suitable for oral, parenteral (including subcutaneous, transdermal, intradermal, intramuscular and intravenous), rectal and topical (including dermal, buccal and sublingual) administration although the most suitable route may depend upon, for example, the condition and disorder of the recipient. The formulations may conveniently be presented in unit dosage form and may be prepared by any of the methods well know in the art of pharmacy. All methods include the step of bringing into association a compound of Formula I or a pharmaceutically acceptable salt, ester amide or solvate thereof (active ingredient) with the carrier which constitutes one or more accessory ingredients. In general the formulations are prepared by uniformly and intimately bringing into association the active ingredients with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion, or a water-in-oil liquid emulsion. The active ingredient may also be presented as a bolus, electuary or paste.

Formulations for parenteral administration include aqueous and non-aqueous sterile injection solutions which may contain anti-oxidants, buffers, bacterioistats and solutes which render the formulation isotonic with the blood of the intended recipient; and aqueous and non-aqueous sterile suspensions which may include suspending agents and thickening agents. The formulations may be presented in unit-dose or multi-dose containers, for Example sealed ampoules and vials, and may be stored in a freeze-dried (lyophillised) condition requiring only the addition of the sterile liquid carrier, for Example, water-for-injection, immediately prior to use. Extemporaneous injection solutions and suspensions may be prepared from sterile powders, granules and tablets of the kind previously described.

Formulations suitable for transdermal administration may be presented as discrete patches adapted to remain in intimate contact with the epidermis of the recipient for a prolonged period of time. Such patches suitably contain the active compound 1) in an optionally buffered, aqueous solution or 2) dissolved and/or dispersed in an adhesive or 3) dispersed in a polymer. A suitable concentration of the active compound is about 1% to 35%, preferably about 3% to 15%. As one particular possibility, the active compound may be delivered from the patch by electrotransport or iontophoresis, as generally described in Pharmaceutical. Res., 3(6), 318 (1986).

Preferred unit dosage formulations are those containing an effective dose, as hereinbelow recited, or an appropriate fraction thereof, of the active ingredient.

It should be understood that in addition to the ingredients particularly mentioned above, the formulations of this invention may include other agents conventional in the art having regard to the type of formulation in question. For example, those suitable for oral administration may include flavoring agents.

For the above-mentioned conditions and disorders, the compounds of the Formula I are preferably administered orally or by injection (intraparenteral or subcutaneous). The precise amount of compound administered to a patient will be the responsibility of the attendant physician. However, the dose employed will depend on a number of factors, including the age and sex of the patient, the precise disorder being treated, and its severity. Also the route of administration is likely to vary depending on the condition and its severity.

In chronic dosing for each of the above-mentioned indications, the compounds of Formula I may be administered orally by tablets or other forms of presentation in discrete units which may contain from about 0.5 mg to 500 mg and generally from about 1 mg to 250 mg of compound. The typical oral dose range for adult humans is from about 1 to 1000 mg/day, and generally from about 5 to 250 mg/day. The compounds of Formula I may be administered by injection at a dose of from about 1 to 1000 mg/day, and generally from about 5 to 1000 mg/day. In clinical situations where acute dosing is appropriate, higher doses of from two to ten times the chronic dose may be utilized.

The present invention further includes processes for the preparation of compounds of Formula I and esters, amides, salts or solvates thereof by the methods hereinafter described, or in any manner known in the art for the preparation of compounds of analogous structure.

Esters and amides of the compounds of the present invention can be made by reaction with a carbonylating agent (e.g., ethyl formate, acetic anhydride, methoxyacetyl chloride, benzoyl chloride, methyl isocyanate, ethyl chloroformate, methanesulfonyl chloride) and a suitable base (e.g., 4-dimethylaminopyridine, pyridine, triethylamine, potassium carbonate) in a suitable organic solvent (e.g., tetrahydrofuran, acetone, methanol, pyridine, N,N-dimethylformamide) at a temperature of 0° C. to 60° C., and preferably 20° C. to 30° C.

Salts of the compounds of Formula I can be made from the free base form by reaction with the appropriate acid.

The following examples are directed to the preparation of representative compounds of the present invention and certain intermediates useful in their preparation. The examples are presented for purposes of illustration only and should not be construed as limiting the scope of the present invention.

EXAMPLE 1

Preparation of 5-iodoisocytosine

Sodium hydroxide pellets (12.72 g) were dissolved in deionized water (318 mL) in a 1 liter round bottom flask and 2-amino-4-hydroxypyrimidine (35.0 g) was added with stirring. After the solids dissolved, iodine flakes (79.95 g) were added in one portion and the mixture was heated to 90–100° C. for approximately 2.5 hours. The mixture was filtered while hot and the solid was washed liberally with water, rinsed with methanol, and dried under vacuum at 115° C. to give 5-iodoisocytosine: 72.5 g.

EXAMPLE 2

Preparation of 4-chloro-2-diisopropylaminomethyleneamino-5-iodopyrimidine

A solution of 4.5 mL of oxalyl chloride in 35 mL of dichloromethane was added dropwise over 25 minutes to an ice water bath-cooled solution of 7.0 mL of N,N-diisopropylformamide in 65 mL of dichloromethane with magnetic stirring. After a few minutes, 4.74 g of 2-amino-4-hydroxy-5-iodopyrimidine was added in one portion. The bath was removed and the solution was stirred at room temperature for 30 minutes, then refluxed for one and one half hours. The solution was cooled and poured into an equal amount of ice-cold saturated aqueous sodium bicarbonate with stirring. The two phases were partitioned and the organic layer washed with additional bicarbonate(2×), water(1×) and finally saturated aqueous brine. After drying over sodium sulfate and filtration, the solution was evaporated in vacuo to yield 10.13 g of a reddish oil. The oil was purified by column chromatography on silica gel, eluting with dichloromethane. Like fractions were pooled, evaporated and triturated with hexanes to give white free flowing crystals, 5.94 g, m.p. 97–100° C.

EXAMPLE 3

Preparation of 4-chloro-5-(4-chlorophenylethynyl)pyrimidine

A mixture of 0.6 g of 1-chloro-4-ethynylbenzene, 1.44 g of 4-chloro-5-iodopyrimidine (J. Chem. Soc. Perkins Trans. I, 1977,621, Allen et al), 7.0 cc of triethylamine, 58 mg of copper iodide and 108 mg of dichlorobis(triphenylphosphine)palladium II was stirred at room temperature under nitrogen for 18 hours. The reaction mixture was evaporated in vacuo. The resulting tan solid was partitioned between water and dichloromethane and the organic extracts washed twice with water, dried over sodium sulfate and evaporated to give a dark brown solid, 1.57 g. The solid was redissolved in dichloromethane and hexanes added to give 120 mg of a beige powder after filtration. The filtrate was purified by column chromatography on silica gel using 1:1 ethyl acetate/dichloromethane as the eluant. The middle rf spot fractions (silica gel TLC in 1:1) were pooled and evaporated to give 0.8 g of a yellow solid, 4-chloro-5-(4-chlorophenylethynyl)-pyrimidine

EXAMPLE 4

Preparation of 5-(4-chlorophenylethynyl)-4-(trans-4-hydroxycyclohexylamino) pyrimidine A mixture of 0.46 g of 4-chloro-5-(4-chlorophenylethynyl)pyrimidine, 3.0 mL of dichloromethane, 3.0 mL of acetonitrile, 1.7 mL of triethylamine and 0.92 g of trans-4-aminocyclohexanol hydrochloride was refluxed for 18 hours. The mixture was evaporated in vacuo and partitioned between dichloromethane and water. The organic phase was washed an additional time with water, dried over sodium sulfate, filtered and evaporated to give 0.54 g of a yellow foam. It was dissolved in dichloromethane and applied to a column of fine mesh silica gel in the same solvent. The column was eluted with 1:1 ethyl acetate/dichloromethane, then the product was eluted with ethyl acetate to yield, after evaporation, 0.53 g of a brittle foam. An aliquot was triturated with ether to give the desired product 5-(4-chlorophenylethynyl)-4-(trans-4-hydroxycyclohexylamino)pyrimidine as a 0.2 M hydrate, m.p. 151–155° C.

EXAMPLE 5

Preparation of 4-chloro-5-phenylethynylpyrimidine

A mixture of 2.1 g of 4-chloro-5-iodopyrimidine, 10 mL of triethylamine, 1.2 mL phenylacetylene, 80 mg copper iodide and 160 mg of dichlorobis(triphenylphosphine was stirred at room temperature for 18 hours. The mixture was diluted with dichloromethane and evaporated in vacuo. The residue was redissolved in a few mL of dichloromethane, 10 mL of triethylamine added and the mixture heated at reflux for one hour. The heterogeneous mixture was evaporated in vacuo and the residue obtained was partitioned between water and dichloromethane. A gelatinous precipitate which formed on shaking the two layers was filtered off, enabling separation of the two layers. The organic extracts were dried over sodium sulfate, filtrated and evaporated in vacuo to yield 2.5 g of a dark brown syrup. The syrup was purified by column chromatography on silica gel, twice, eluting with hexanes, 1:1 hexanes/dichloromethane, dichloromethane and finally ethyl acetate. Like fractions from dichloromethane elution were pooled, obtaining 350 mg of the product, 5-phenylethynyl-4-chloropyrimidine as an oil which solidified to white rosettes.

EXAMPLE 6

Preparation of 4-(trans-4-hydroxycyclohexylamino)-5-phenylethynylpyrimidine

A mixture of 0.2 g of 5-phenylethynyl-4-chloropyrimidine, 10 mL of acetonitrile, 0.42 g of trans aminocyclohexanol and 0.4 mL of triethylamine was refluxed overnight with magnetic stirring. The mixture was cooled and filtered and the filtrate evaporated in vacuo. The residue was purified by column chromatography on silica gel, eluting successively with dichloromethane, 1:1 dichloromethane and finally ethyl acetate. The product, 4-(trans-4-hydroxycyclohexylamino)-5-phenylethynylpyrimidine, 200 mg, was obtained on evaporation of the latter eluate.

EXAMPLE 7

Preparation of 4-chloro-2-diisopropylaminomethyleneamino-5-phenylethynylpyrimidine A mixture of 2.46 g 4-chloro-2-diisopropylaminomethyleneamino-5-iodopyrimidine, 7.5 mL triethylamine, 0.064 g copper iodide, 0.12 g dichlorobis(triphenyl)phosphine palladium II and 0.9 mL phenylacetylene was stirred under nitrogen at room temperature for two days. The dark brown mixture was evaporated in vacuo at a bath temperature of 30–35° C. The residue was partitioned between dichloromethane and water. The organic phase was washed thrice with water, dried over sodium sulfate, filtered and evaporated to yield 3.37 g of a dark brown oil. The residue was dissolved in hexanes and purified by column chromatography on silica gel, eluting successively with hexanes, 1:1 dichloromethane/hexanes and dichloromethane. The product was obtained from the latter eluant to yield after evaporation, 1.69 (74%) g of 4-chloro-2-diisopropylaminomethyleneamino-5-phenylethynylpyrimidine.

EXAMPLE 8

Preparation of 2-diisopropylaminomethyleneamino-4-(trans-4-hydroxycyclohexylamino-5-phenylethynylpyrimidine A mixture of 0.5 g of 4-chloro-2-diisopropylaminomethyleneamino-5-phenylethynylpyrimidine, 15 mL of acetonitrile, 0.67 g of trans 4-aminocyclohexanol hydrochloride and 1.8 mL of triethylamine was refluxed with magnetic stirring 18 hours. The mixture was chilled, filtered and the precipitate washed with acetonitrile. The filtrate was evaporated in vacuo and the resulting rust colored residue dissolved in dichloromethane. The solution was loaded on a column of fine mesh silica gel. The column was eluted with dichloromethane, then successively with 10%, 30%, 60% ethyl acetate in dichloromethane, ethyl acetate and finally 10% methanol in dichloromethane. Recovered starting material, 4-chloro-2-diisopropylaminomethyleneamino-5-phenylethynylpyrimidine, 0.180 g was obtained on evaporation of the 10% ethyl acetate eluate. The product, 2-diisopropylaminomethyleneamino-4-trans-4-hydroxycyclohexylamino-5-phenylethynylpyrimidine, 0.32 g, was obtained from evaporation of the 60% and subsequent eluates.

EXAMPLE 9

Preparation of 2-amino-4-(trans-4-hydroxycyclohexylamino)-5-phenylethynylpyrimidine A solution of 0.24 g of 2-diisopropylaminomethyleneamino-4-(trans-4-hydroxycyclohexylamino-5-phenylethynyl-pyrimidine in 5.0 mL each of ethanol and 4% aqueous sodium hydroxide was refluxed for 18 hours. The solution was evaporated in vacuo and the residue extracted with dichloromethane. The extracts were washed with water and dried over sodium sulfate. The filtered solution was loaded on a column of fine mesh silica gel in the same solvent. After washing the column with dichloromethane and acetonitrile, the product was eluted with 5% and 10% methanol in dichloromethane, to obtain on evaporation 0.1 g of a brittle foam. The product was converted to the hydrochloride by addition of ethanolic HCl to a solution of the base in 1:1 ether-ethanol to a pH of 2.0. The resulting solution was evaporated in vacuo and triturated with acetone and dried to yield 0.063 g of a yellow solid, one spot by TLC (10% methanol in dichloromethane).

EXAMPLE 10

Preparation of 4-chloro-5-(4-chlorophenylethynyl)-2-diisopropylaminomethyleneamino-pyrimidine A mixture of 0.722 g 4-chloro-2-diisopropylaminomethyleneamino-5-iodopyrimidine, 3.5 mL triethylamine, 0.025 g copper iodide, 0.037 g dichlorobis(triphenyl)phosphine palladium II and 0.289 g 1-chloro-4-ethynylbenzene was stirred under nitrogen at room temperature for 18 hours. The dark brown mixture was evaporated in vacuo at a bath temperature of 30–35° C. The beige residue was partitioned between dichloromethane and water. The organic phase was washed twice with water, dried over sodium sulfate, filtered and evaporated to yield 1.0 g of a caramel colored film. The residue was dissolved in 1:1 dichloromethane/hexanes and purified by column chromatography on silica gel, eluting successively with 1:1 dichloromethane/hexanes, dichloromethane and ethyl acetate. The product was recovered from the latter two eluates by evaporation to yield 0.7 g of 4-chloro-5-(4-chlorophenylethynyl)-2-diisopropylaminomethyleneaminopyrimidine.

EXAMPLE 11

Preparation of 5-(4-chlorophenylethynyl)-2-diisopropylaminomethyleneamino-4-(trans-4-hydroxycyclohexylamino) pyrimidine A mixture of 0.46 g of 4-chloro-5-(4-chlorophenylethynyl)-2-diisopropylaminomethyleneamino-pyrimidine, 15 mL of acetonitrile, 2 mL of triethylamine and 0.56 g of trans-4-aminocyclohexanol hydrochloride was refluxed 18 hours with magnetic stirring. The mixture was chilled, filtered and the precipitate washed with acetonitrile. The filtrate was evaporated in vacuo and the resulting rust colored residue dissolved in dichloromethane. The solution was loaded on a column of fine mesh silica gel. The column was eluted with dichloromethane, yielding 0.19 g of starting material, 5-(4-chlorophenylethynyl)-2-diisopropylaminomethyleneamino-4-chloropyrimidine, with ethyl acetate and finally 10% methanol in dichloromethane to give 0.53 g of 5-(4-chlorophenylethynyl)-2-diisopropylaminomethyleneamino-4-(trans-4-hydroxycyclohexylamino)-pyrimidine. The $^1$H NMR spectrum (CDCl3) was consistent with the structure.

EXAMPLE 12

Preparation of 2-amino-5-(4-chlorophenylethynyl)-4-(trans-4-hydroxycyclohexylamino)pyrimidine A mixture of 1.25 g of 4-chloro-5-(4-chlorophenylethynyl)-2-diisopropylaminomethyleneamino-pyrimidine, 33 mL of ethanol, 2.02 g of trans-4-aminohexanol hydrochloride and 1.9 mL of triethylamine was stirred at reflux for three days. The clear amber solution was evaporated in vacuo and the beige solid was partitioned between dichloromethane and water. A portion of the solid insoluble in either phase was filtered off. It weighed 0.24 g and was identical on TLC(silica gel in ethyl acetate) to the product obtained from the organic phase. The organic phase was dried over sodium sulfate, filtered and evaporated in vacuo to give 0.67 g. Purification of the latter by column chromatography on silica gel was effected by first eluting the column with dichloromethane and 50% ethyl acetate in dichloromethane. Elution with ethyl acetate and evaporation yielded 190 mg of the desired product, 2-amino-5-(4-chlorophenylethynyl)-4-(trans-4-hydroxycyclohexylamino)pyrimidine. An analytical sample was obtained by recrystallization of the material filtered from the reaction from 2-propanol and water, 0.19 g. m.p. 215–218° C.,

EXAMPLE 13

Preparation of 2-amino-5-(4-chlorophenylethynyl)-4-(2-hyroxyethylamino) pyrimidine A mixture of 0.7 g of 4-chloro-5-(4-chlorophenylethynyl)-2-diisopropylaminomethyleneamino-pyrimidine, 20 mL ethanol and 0.6 mL ethanolamine was refluxed for 18 hours. The green solution was evaporated in vacuo and triturated with water. The insoluble yellow residue was recrystallized by dissolving in 35 mL hot methanol, concentrating to 10 mL and chilling. The pale yellow powdery precipitate was filtered and dried to yield 0.34 g of 2-amino-5-(4-chlorophenylethynyl)-4-(2-hyroxyethylamino)pyrimidine, m.p. 197–200° C.

EXAMPLE 14

Preparation of 2-amino-5-(4-chlorophenylethynyl)-4-[2-(2-hydroxyethoxy)ethylamino]pyrimidine A mixture of 0.3 g of 4-chloro-5-(4-chlorophenyl)-ethynyl-2-diisopropylaminomethyleneamino-pyrimidine, 6.0 mL ethanol and 0.26 g of 2-(2-aminoethyoxy)ethanol was refluxed for 18 hours. The reaction mixture was evaporated in vacuo, the yellow solid dissolved in dichloromethane and loaded on a column of silica gel in the same solvent. The column was eluted successively with dichloromethane, 5% and 10% methanol/dichloromethane. The product 0.15 g was obtained from evaporation of the 10% eluate as a pale yellow solid. Recrystallization from boiling methanol gave 0.17 g of 2-amino-5-(4-chlorophenylethynyl)-4-[2-(2-hydroxyethoxy]ethylamino]pyrimidine. m.p. 176–180° C.

EXAMPLE 15

Preparation of 4-(4-acetylpiperazino)-2-amino-5-(4-chlorophenylethynyl) pyrimidine A mixture of 0.8 g of 4-chloro-5-(4-chlorophenylethynyl)-2-diisopropylaminomethyleneamino-pyrimidine, 35 mL acetonitrile and 0.71 g 1-acetyl piperazine was refluxed for one and one half hours. A green solution initially forms and the color changes to amber on continued heating. The solution was evaporated in vacuo and partitioned between dichloromethane and water. The organic phase was washed twice with water, dried over sodium sulfate, filtered and evaporated. The orange-brown brittle foam obtained was purified by column chromatography on silica gel, eluting initially with dichloromethane and then with 15% methanol/dichloromethane to give the intermediate derivative, 4-(-4-acetyl piperazino)-5-(4-chlorophenylethynyl)-2-diisopropylaminomethyleneaminopyrimidine. Heating 0.6 g of the intermediate with 40 mL methanolic ammonia in a bomb at 120° C. for 18 hours gave on evaporation in vacuo, a cocoa-colored residue which was purified by column chromatography on silica gel. The desired product 4-(4- acetylpiperazino)-2-amino-5-(4-chlorophenylethynyl)pyrimidine was obtained by elution with 5% methanol/dichloromethane, evaporation and trituration with methanol yielding 0.27 g, m.p. 165° C.

EXAMPLE 16

Preparation of 2-amino-5-(4-chlorophenylethynyl)-4-(4-hydroxyanilino)pyrimidine

A mixture of 0.932 mM of 5-(4-Chlorophenylethynyl)-2-diisopropylaminomethyleneamino-4-chloropyrimidine and 0.102 g of 4-aminophenol in 5 mL ethanol was stirred at room temperature for four days.

The brown solution was evaporated in vacuo (bath temperature 30° C.) to obtain a brownish-burgundy solid. The residue was stirred in dichloromethane and filtered to yield 0.4 g of 5-(4-chlorophenylethynyl)-2-diisopropylaminomethyleneamino-4-(4-hydroxyanilino)pyrimidine. The $^1$H NMR spectrum (CDCL$_3$) was consistent with this structure. A mixture of 0.37 g of this product was heated in a bomb with 32 mL of methanolic ammonia at a temperature of 100° C. for five hours. The cooled bomb contents were evaporated in vacuo and triturated with ice cold water and dried to yield a mixture of the desired 2-amino-5-(4-chlorophenylethynyl)-4-(4-hydroxyanilino)pyrimidine with 2,4-diamino-5-(4-chlorophenylethynyl)pyrimidine.

EXAMPLE 17

Preparation of 5-(4-chlorophenylethynyl)-2-diisopropylaminomethyleneamino-4-morpholinopyrimidine A mixture of 0.46 g of 4-chloro-2-diisopropylaminomethyleneamino-5-(4-chlorophenylethynyl)-pyrimidine, 40 mL of acetonitrile and 0.41 g of morpholine was stirred at room temperature for 18 hours. The mixture was evaporated in vacuo and the residue partitioned between water and dichloromethane. The organic layer was washed once more with water, dried over sodium sulfate and filtered. The filtrate was loaded on a column of silica gel equilibrated in the same solvent. After elution of an unknown impurity, the product eluted as a yellow band. Additional material was obtained by a final elution with 1:1 dichloromethane and ethyl acetate. Like fractions of the two eluants were pooled and evaporated to give 0.63 g of a yellow oil, 5-(4-Chlorophenylethynyl)-2-diisopropylaminomethyleneamino-4-morpholinopyrimidine.

EXAMPLE 18

Preparation of 2-amino-5-(4-chlorophenylethynyl)-4-morpholinopyrimidine

A solution of 0.63 g of 5-(4-chlorophenylethynyl)-2-diisopropylaminomethyleneamino-4-morpholinopyrimidine and 35 mL of freshly prepared saturated methanolic ammonia was heated in a bomb at 60° C. for 18 hours. The bomb was cooled, opened and the yellow solution was cooled. A precipitate formed which was filtered to give 0.2 g of a yellow solid. Thin layer chromatography (silica gel in 20% ethyl acetate in dichloromethane) showed the filtrate displayed two spots, the upper one corresponding to the starting material and the lower to the precipitate. The latter was homogeneous and its $^1$H-NMR (DMSO-d$_6$) was consistent with the desired product, 2-amino-5-(4-chlorophenylethynyl)-4-morpholinopyrimidine. The filtrate was evaporated and recharged with methanolic ammonia in a bomb at 80° C. for 18 hours. After a similar workup, an additional crop, 0.16 g of 2-amino-5-(4-chlorophenylethynyl)-4-morpholinopyrimidine was obtained. Analytical samples as lustrous champagne colored flakes were obtained by recrystallization from boiling MeOH, m.p. 193–194° C.

EXAMPLE 19

Preparation of 2-amino-4-[2-(2-hydroxyethoxy)ethylamino]-5-phenylethynyl pyrimidine A mixture of 1.5 g of 4-chloro-2-diisopropylaminomethyleneamino-5-phenylethynylpyrimidine, 20 mL of ethanol and 1.83 g of 2-(2-aminoethoxy)ethanol was refluxed for 18 hours. The tea colored solution was evaporated in vacuo and the residue partitioned between water and dichloromethane. The aqueous layer was washed twice more with dichloromethane and the combined organic extracts washed with water. The organic solution was dried over sodium sulfate, filtered and evaporated in vacuo. The yellow residue obtained was triturated with ether and filtered to give 0.49 g of a yellow solid, 2-amino-4-[2-(2-hydroxyethoxy)ethylamino]-5-phenylethynylpyrimidine. m.p. 128–129° C.

EXAMPLE 20

Preparation of 4-(4-hydroxyanilino)-5-phenylethynylpyrimidine hydrochloride

A mixture of 0.23 g of 4-chloro-5-(4-phenylethynyl) pyrimidine, 8 mL of ethanol and 0.12 g of 4-hydroxyaniline was stirred at room temperature for 18 hours. The heterogeneous mixture was filtered, washed with ether and dried to yield 0.189 g of a yellow powder 4-(4-hydroxyanilino)-5-phenylethynylpyrimidine hydrochloride, m.p. 223–225° C., with decomposition.

EXAMPLE 21

Preparation of 5-(4-chlorophenylethynyl)-4-(4-hydroxyanilino)pyrimidine hydrochloride A mixture of 0.28 g of 4-chloro-5-(4-Chlorophenylethynyl)pyrimidine, 10 mL of ethanol and 0.14 g of 4-hydroxyaniline was stirred at room temperature for 18 hours. The black mixture was evaporated in vacuo and the residue was triturated with dichloromethane, ethylacetate and acetonitrile. The combined organic extracts were absorbed on silica gel and evaporated in vacuo. The powder was added to a column of silica gel equilibrated in dichloromethane and eluted with the same solvent. The column was eluted with ethyl acetate and then 10% methanol in dichloromethane. These eluates on evaporation produced 100 mg of the 5-(4-chlorophenylethynyl)-4-(4-hydroxyanilino)pyrimidine hydrochloride as a muddy yellow powder.

EXAMPLE 22

Preparation of 2-amino-5-(4-chlorophenylethynyl)-4-(4-oxocyclohexylamino) pyrimidine Oxalyl chloride (1.52 g) and dichloromethane (50 mL) were combined under a nitrogen atmosphere and cooled to −78° C. in a dry ice-acetone bath. Dimethyl sulfoxide (1.88 g) was added dropwise via syringe through a rubber septum cap. After completion of the addition, solid 2-amino-5-(4-chlorophenylethynyl)-4-(4-trans-hydroxycyclohexylamino) pyrimidine (3.43 g) was added in one portion and the mixture was stirred for 30 minutes. Triethylamine (7 mL)

was added in portions via syringe and after completion of the addition the cooling bath was removed and the mixture was allowed to warm to room temperature. The mixture was poured into water (40 mL) and the organic phase was separated; it was washed with water (1×50 mL), brine (1×50 mL), dried over sodium sulfate, filtered and stripped in vacuo to a yellow foam. The product was purified by chromatography on silica gel (30 g) using a mixture of dichloromethane and ethyl acetate. Fractions corresponding to the desired product were pooled and stripped in vacuo to give 2-amino-5-(4-chlorophenylethynyl)-4-(4-oxocylohexylamino)pyrimidine as a yellow powder: 2.32 g; m.p. 176–178C.

EXAMPLE 23

Preparation of 2-amino-5-(4-chlorophenylethynyl)-4-(4-cis-hydroxycyclohexylamino)pyrimidine 2-Amino-5-(4-chlorophenylethynyl)-4-(4-oxocyclohexylamino)pyrimidine (1.02 g) was dissolved in sodium dried tetrahydrofuran (100 mL) under a nitrogen atmosphere and the mixture was cooled to −78° C. in a dry ice-acetone bath. Lithium tri-sec-butylborohydride (6 mL, 1.0 mM in THF) was added via syringe through a rubber septum cap and the mixture was stirred for 1.5 hours. The reaction mixture was quenched by addition of saturated aqueous ammonium chloride solution (8 mL) at −78° C. and then warmed to approximately 10–15° C. and decanted from the white solids which had formed. The solids were washed with dichloromethane and the combined filtrates were stripped in vacuo and redissolved in dichloromethane. The solution was washed with 2 M sodium hydroxide (1×50 mL), brine (1×50 mL), dried over sodium sulfate, filtered and stripped in vacuo to a foam. The cis/trans mixture of amino alcohols was purified by chromatography on silica gel (10 g) using methylenechloride/acetone as eluent. Fractions containing the cis-amino alcohol by tlc were pooled and stripped in vacuo and the residue was crystallized from 95% aqueous ethanol to give 2-amino-5-(4-chlorophenylethynyl)-4-(4-cis-hydroxycyclohexylamino)pyrimidine as light yellow plates; 458.4 mg; m.p. 186–187° C.

EXAMPLE 24

Preparation of 4-ethyl-1-ethynylbenzene

A mixture of 5.6 mL of 1-ethyl-4-iodobenzene, 75 mL of triethylamine, 6 mL of trimethylsilylacetylene, 0.49 g of dichlorotriphenylphosphine palladium II and 0.314 g copper iodide was magnetically stirred at ambient temperature for 18 hrs. The thick dark brown mixture was filtered, washing the gray precipitate with hexanes. The filtrate and washings were evaporated in vacuo and the residue dissolved in hexanes. This solution was 96.7% pure by GC analysis. The solution was passed down a column of silica gel which had been equilibrated in the same solvent and the eluates evaporated in vacuo to yield 9.3 g of 4-ethyl-1-trimethylsilyl ethynylbenzene as a dark amber liquid.

The residue was dissolved in 50 mL of methanol and stirred with 0.55 g of potassium carbonate at room temperature for 2.5 hrs. The mixture was evaporated in vacuo with the bath temperature at 60° C. The resulting dark residue was partitioned between dichloromethane and water, the organic phase washed with 0.1N aqueous HCl and filtered off some sludge from the organic phase. The extracts were dried over sodium sulfate, filtered and flash evaporated to give a dark brown liquid. The liquid was stirred in hexanes, filtered and loaded on a column of silica gel in hexanes. Elution with this solvent gave a colorless solution, which on flash evaporation gave 3.44 g of 4-ethyl-1-ethynylbenzene as a pale yellow liquid, GC purity 99.4%.

EXAMPLE 25

Preparation of 4-chloro-2-diisopropylaminomethyleneamino-5-(4-ethylphenylethynyl)pyrimidine A mixture of 6.3 g of 4-chloro-2-diisopropylaminomethyleneamino-5-iodopyrimidine, 33 mL of triethylamine, 2.43 g of 4-ethyl-1-ethynylbenzene, 0.304 g of dichlorobis(triphenyl)phosphine palladium II and 0.21 g copper iodide was magnetically stirred at reflux temperature for 1.5 hrs. The mixture was filtered and the filtrate evaporated in vacuo. Both the precipitate and the evaporated filtrate were dissolved in dichloromethane and washed with water, dried over sodium sulfate, filtered and evaporated. The residues were dissolved in 1:1 dichloromethane-hexanes and separately purified by column chromatography. After initial elution with 1:1 dichloromethane-hexanes, the product was obtained by elution with dichloromethane and 50% ethyl acetate-dichloromethane. Evaporation of the eluates gave 4.04 g of 4-chloro-2-diisopropylaminomethyleneamino-5-(4-ethylphenylethynyl)pyrimidine as a thick amber syrup.

EXAMPLE 26

Preparation of 2-amino-5-(4-ethylphenylethynyl)-4-(4-trans-hydroxycyclohexylamino) pyrimidine hydrochloride A mixture of 1.925 mM of 4-chloro-2-diisopropylaminomethyleneamino-5-(4-ethylphenyl) ethynylpyrimidine and 0.89 g of trans 4-aminocyclohexanol in 5.0 mL of absolute ethanol was heated in a bomb at 120° C. for 18 hours. After removal, the dark amber bomb solution was evaporated in vacuo and co-evaporated with acetone. The residue was washed with water and the water insoluble material flash evaporated with acetone. The residue was dissolved in 5% methanol in dichloromethane and applied to a column of silica gel in the same solvent. Evaporation of the 5% eluates provided 600 mg of a tan solid which was dissolved in ethanol and acidified with EtOAc-HCl to a pH of 1.0. Addition of excess ether and chilling gave 0.21 g of 2-amino-5-(4-ethylphenylethynyl)-4-(4-trans-hydroxycyclohexylamino)pyrimidine hydrochloride. m.p. 240–255° C.

EXAMPLE 27

Preparation of 5-(4-bromophenylethynyl)-4-chloro-2-diisopropylaminomethyleneaminopyrimidine A mixture of 0.5 g of 1-bromo-4-ethynylbenzene, 5.0 mL of triethylamine, 0.031 mg of copper iodide, 0.94 g of 4-chloro-2-diisopropylaminomethyleneamino-5-iodopyrimidine and 0.046 g of dichlorobis(triphenyl)phosphine palladium II was magnetically stirred at room temperature for 18 hrs. The mixture was diluted with acetonitrile, filtered and the filtrate evaporated in vacuo. The evaporated filtrate was dissolved in dichloromethane and loaded on a column of silica gel equilibrated in the same solvent. Cuts were monitored by thin layer chromatography. After initial cuts of brown colored eluates, the product subsequently eluted as yellow fractions. Like cuts were pooled and evaporated to give 0.84 g of 5-(4-bromophenylethynyl)-4-chloro-2-diisopropylaminomethyleneaminopyrimidine as a thick amber syrup.

EXAMPLE 28

Preparation of 2-amino-5-(4-bromophenylethynyl)-4-(4-trans-hydroxycyclohexylamino)pyrimidine hydrochloride A mixture of 1.3 g of 5-(4-bromophenylethynyl)-4-chloro-2-diisopropylaminomethyleneamino-pyrimidine and 1.48 g of trans 4-amino-cyclohexanol in 16 mL of absolute ethanol was refluxed for 18 hrs. The solvent was distilled off at atmospheric pressure and the residue cooled and triturated with water. The water insoluble residue was dissolved in methanol and azeotropically dried by co-evaporation (flash) with acetone. The olive green residue was dissolved in methanol, preabsorbed on silica gel, evaporated and applied to a column of silica gel equilibrated in ethyl acetate. The product was eluted with ethyl acetate and evaporated to give a pale green foamy residue, 0.74 g of 2-amino-5-(4-bromophenylethynyl)-4-(4-trans-hydroxy cyclohexylamino) pyrimidine The solid was recrystallized from a minimum amount of boiling ethanol and chilled. A small amount of precipitate was obtained (80 mg) of an unknown substance, which was different by TLC from the filtrate. The pH of the filtrate was adjusted to 2.0 with HCl in EtOAC and the solution evaporated in vacuo to give a yellow solid. The solid was triturated with ether and filtered to give 0.69 g of a buttermilk powder. The solid was triturated with water to remove any amine hydrochloride, then dried. The material, 0.23 g analyzed as the anhydrous salt 2-amino-5-(4-bromophenylethynyl)-4-(4-trans-hydroxycyclohexylamino)pyrimidine hydrochloride, m.p 240° C. with decomposition.

EXAMPLE 29

Preparation of 1-acetamido-4-ethynylbenzene

A mixture of 1.0 g of 4-ethynylaniline and 2.4 mL of acetic anhydride in 5.0 mL of dichloromethane was stirred at room temperature for 18 hours. The solution was evaporated in vacuo at 40° C. The resulting semi solid mixture was suspended in hexanes and filtered. The hexanes filtrate was washed twice with water and dried over sodium sulfate. After filtering it was combined with the hexanes insoluble residue, dissolved in dichloromethane and purified by column chromatography in the same solvent to yield 0.96 g of 1-acetamido-4-ethynylbenzene.

EXAMPLE 30

Preparation of 5-(4-acetamidophenylethynyl)-4-chloro-2-diisopropylaminomethyleneamino-pyrimidine The compound was prepared following the general method of Example 27 with the addition of acetonitrile as a reaction solvent.

Example 31

Preparation of 5-(4-acetamidophenylethynyl)-2-amino-4-(4-trans-hydroxycyclohexylamino)-pyrimidine hydrochloride The compound was prepared following the general method of Example 28. m.p. 238–245° C. with decomposition.

EXAMPLE 32

Preparation of 4-chloro-2-dimethylaminomethyleneamino-5-iodopyrimidine

N,N-dimethylformamide (54.1 g) and dry acetonitrile (500 mL) were combined under nitrogen in a 4 liter round bottom flask. Oxalyl chloride (93.9 g) was added dropwise over a 1 hour period to form the intermediate Vilsmeier reagent and the HCl was vented through an aqueous sodium hydroxide scrubber. Solid 5-iodoisocytosine (77 g, 0.32 moles) was added in one portion and the mixture was heated at 60° C. for approximately 3 hours. The mixture was cooled to about 25° C. and the solids were filtered and washed with acetonitrile. The filter cake was slurried with deionized water (500 mL) and sodium bicarbonate (29 g) was added to maintain pH 8. The solids were filtered, washed with water, and dried in vacuo at 50° C. to give 4-chloro-2-dimethylaminomethyleneamino-5-iodopyrimidine: 88 g m.p. 99–100° C.

EXAMPLE 33

Preparation of 4-chloro-5-(4-chlorophenylethynyl)-2-dimethylaminomethyleneaminopyrimidine A 1-liter, 3-neck-round-bottom flask was equipped with an air stirrer, reflux condenser, and a nitrogen inlet. The 4-chloro-2-(dimethylaminomethyleneamino)-5-iodopyrimidine (65.2 g), ethanol (84 mL), and triethylamine (336 mL) were charged and heated to reflux. Copper (I) iodide (105 mg) and dichlorobis(triphenyl)phosphine palladium II (386 mg) were added. Neat 1-chloro-4-ethynylbenzene (30.1 g) was added and the mixture was refluxed approximately 2.5 hours. The mixture was cooled to ambient temperature, stirred for 1.5 hours and filtered. The filter cake was slurried in water:ethanol (4:1 v/v, 120 mL), filtered and dried in vacuo at 50° C. to give 4-chloro-5-(4-chlorophenylethynyl)-2-dimethylaminomethyleneaminopyrimidine as a yellow solid: 55.7 g m.p. 195–197° C.

EXAMPLE 34

Preparation of 4-chloro-5-(4-chlorophenylethynyl)-2-formamidopyrimidine

4-Chloro-5-(4-chlorophenylethynyl)-2-dimethylaminomethyleneaminopyrimidine (65.1 g), isopropanol (585 mL), and water (36 mL) were combined and warmed to 60° C. Methane sulfonic acid (23.1 g) was added and heating at 60oC was continued for 1.5–2.0 hours or until HPLC analysis confirmed the absence of the starting material. The mixture was cooled to ambient temperature and held for 1.5 hours. The solids were removed by filtration and washed with isopropanol (100 mL). The filter cake was slurried in water (500 mL), basified with 1 N NaOH to pH 11, filtered, and the solids were rinsed with water. Vacuum drying at 50° C. provided predominantly 4-chloro-5-(4-chlorophenylethynyl)-2-formamidopyrimidine: 51.6 g.

EXAMPLE 35

Preparation of 2-amino-5-(4-chlorophenylethynyl)-4-(4-trans-hydroxycyclohexylamino)pyrimidine 4-Chloro-5-(4-chlorophenylethynyl)-2-formamidopyrimidine (42.9 g), n-propanol (344 mL), and trans-4-aminocyclohexanol (51.7 g) were combined and heated to reflux. HPLC analysis confirmed that the reaction was complete in approximately 4 hours. The mixture was cooled and held at ambient temperature for 1.5 hours and the yellow solids were filtered and washed with ethanol (200 mL). The filter cake was slurried in water (250 mL), adjusted to pH 10 with 1N NaOH, and filtered. The filter cake was washed with water (200 mL) and dried in vacuo at 50° C. to give 2-amino-5-(4-chlorophenylethynyl)-4-(4-trans-hydroxycyclohexylamino)pyrimidine: 41.2 g m.p. 216–218° C.

EXAMPLE 36

Preparation of 2-amino-4-(4-trans-hydroxycyclohexylamino)-5-(4-nitrophenylethynyl)pyrimidine hydrochloride The compound was prepared in two steps by the methods of example 17 (at reflux temperature, 3.5 hrs) and example 12 (using four equivalents of the free base of 4-trans hydroxycyclohexylamine, in refluxing n-propanol, 18 hrs). m.p. 255° C.

EXAMPLE 37

Preparation of 2-amino-4-(4-trans-hydroxycyclohexylamino)-5-(4-propylphenylethynyl)pyrimidine hydrochloride A mixture of 5.0 g of 4-bromopropylbenzene, 15 mL of dichloromethane, 0.64 g of copper iodide, 0.32 g of dichlorobis(triphenyl)phosphine palladium II, 3.7 mL of trimethylsilylacetylene and 12.3 mL of triethylamine was refluxed for 18 hrs. The mixture was evaporated in vacuo (bath temperature 48° C.). The dark residue was dissolved in hexanes and passed through a pad of silica gel, washing the column well with additional solvent. The eluates were evaporated, redissolved in hexanes and purified on a column of silica gel in the same solvent. The fractions were monitored by thin layer chromatography. The initial cut contained two spots, the next a trace of the upper spot and the subsequent ones only the lower spot. The latter two were evaporated separately and analyzed by GC showing. 66 and 86% purity respectively. These eluates were combined and evaporated in vacuo to give 3.0 g of 1-propyl-4-trimethylsilybenzene. The liquid was combined with 10 mL of methanol and 0.16 g of potassium carbonate and stirred at room temperature for three hours. The mixture was partitioned between hexanes and 0.5 N aqueous HCl. The organic layer was washed twice with water and dried over sodium sulfate. Evaporation of the filtered extracts gave 1.96 g of a honey colored liquid, 1-ethynyl-4-n-propylbenzene, 75.8% purity by GC.

The subsequent steps in the preparation of the subject compound followed the general procedure of Example 33, giving 90 mg of 2-amino-4-(4-trans-hydroxycyclohexylamino)-5-(4-propylphenylethynyl)pyrimidine hydrochloride, m.p. 198–200° C.

EXAMPLE 38

Preparation of 2-amino-4-(4-hydroxyanilino)-5-(4-methoxyphenylethynyl)pyrimidine hydrochloride The compound was prepared following the general procedures of examples 8 and 16. The diisopropylmethine protecting group on the 2-amino substituent was removed by refluxing in ethanol with three equivalents of 6 N aqueous HCl for one hour to give 2-amino-4-(4-hydroxyanilino)-5-(4-methoxyphenylethynyl)pyrimidine hydrochloride. m.p. 220–230° C. with decomposition.

EXAMPLE 39

Preparation of 2-amino-5-(4-chlorophenylethynyl)-4-(4-trans-hydroxycyclohexylamino)pyrimidine-O-dimethylphosphate 2-Amino-5-(4-chlorophenylethynyl)-4-(4-trans-hydroxycyclohexylamino)pyrimidine (3.43 g) was dissolved in dry tetrahydrofuran (150 mL) under nitrogen. The solution was cooled to −78° C. in a dry ice/acetone bath and a solution of lithium diisopropylamide (5.2 mL, 2.0 mM in THF) was added in portions. After an additional one hour, dimethylchlorophosphate (1.52 g) was added, the cooling bath was removed, and the mixture was allowed to warm to ambient temperature and stir overnight. The mixture was stripped in vacuo and the residue was partitioned between dichloromethane:ethyl acetate (200 mL, 3:1 v/v) and washed with saturated aqueous sodium bicarbonate (50 mL). The organic phase was separated, dried (Na$_2$SO$_4$), filtered, and stripped in vacuo. The residue was purified by chromatography on aluminum oxide (grade I, neutral) using ethyl acetate as eluent. Homogeneous fractions by tic were pooled and stripped in vacuo to give 1.68 g. 2-amino-5-(4-chlorophenylethynyl)-4-(4-trans-hydroxycyclohexylamino)pyrimidine-O-dimethyl phosphate as a yellow foam.

Example 40

Preparation of 5-(4-chlorophenylethynyl)-2-formamido-4-(4-oxocyclhexyloxy)pyrimidine ethylene ketal 1,4-Dioxaspiro[4,5]decane-8-ol (1.74 g) was dissolved in dry dimethylformamide (40 mL) under a nitrogen atmosphere and sodium hydride (440 mg, 60% oil dispersion) was added. 4-Chloro-5-(4-chlorophenylethynyl)-2-dimethylaminomethyleneaminopyrimidine (3.19 g) was then added in one portion after hydrogen evolution had subsided. The mixture was stirred for 2 hours, stripped in vacuo, and the oily residue was redissolved in ethyl acetate (250 mL). The solution was washed with water (3×200 mL), brine (1×200 mL), dried (Na$_2$SO$_4$), filtered, and stripped in vacuo. The residue was dissolved in dichloromethane and purified by chromatography on silica gel (50 g) with a dichloromethane/ethyl acetate gradient. Fractions containing the product by tic were pooled and stripped in vacuo. The residue was recrystallized from hot ethyl acetate to give 1.89 g. of 5-(4-chlorophenylethynyl)-2-formamido-4-(4-oxocyclohexyloxy)pyrimidine ethylene ketal.

EXAMPLE 41

Preparation of 2-amino-5-(4-chlorophenylethynyl)-4-(4-oxocyclohexyloxy) pyrimidine 5-(4-Chlorophenylethynyl)-2-formamido-4-(4-oxocyclohexyloxy)pyrimidine ethylene ketal (1.66 g) was dissolved in tetrahydrofuran (75 mL) and 6M aqueous hydrochloric acid (10 mL). The mixture was stirred at ambient temperature for 3 hours and stripped in vacuo. The residue was partitioned between water and ethyl acetate (150 mL) and basified with 2M aqueous sodium hydroxide. The organic phase was washed with water (1×100 mL), brine (1×100 mL), dried (Na$_2$SO$_4$), filtered, and stripped in vacuo. The residue was recrystallized from hot 2-propanol to give 2-amino-5-(4-chlorophenylethynyl)-4-(4-oxocyclohexyloxy)pyrimidine: 0.88 g; m.p. 168–172° C.

EXAMPLE 42

Preparation of 2-amino-5-(4-chlorophenylethynyl)-4-[2-(2-hydroxyethoxy)ethoxy]pyrimidine 11 g of Diethylene glycol and 0.78 g of a 60% suspension of sodium hydride in mineral oil were stirred in 200 ml of tetrahydrofuran (dried over sieves) for 15 minutes then 1.3 g of 4-chloro-5-(4-chlorophenylethynyl)-2-formamido-pyrimidine was added and the mixture was stirred at 25° C. in a dry atmosphere (drying tube) for 40 hours. The reaction mixture was then evaporated under reduced pressure at 55° C. The resulting syrup was stirred with 250 ml of ethyl acetate, 125 ml of saturated aqueous sodium bicarbonate and 125 ml of water for 15 minutes. The organic phase was washed with 250 ml of water and then 100 ml of brine. After drying over sodium sulfate, the filtered solution was combined with 16 g of Silica gel 60 (230–400 mesh) and evaporated under reduced pressure. The solids were applied to column of silica gel 60 (2.5×9.5 cm). The final height of the column was 16 cm. After eluting the column with increasing concentrations of ethyl acetate in dichloromethane, the product-rich fractions were combined and the solvent evaporated under reduced pressure. The product was recrystallized twice from ethyl acetate to give 0.75 g of the desired product, m.p. 142–143° C.

EXAMPLE 43

Preparation of 2-amino-5-(4-chlorophenylethynyl)-4-(4-hydroxyphenoxy) pyrimidine The compound was prepared following the general method of Example 42 substituting hydroxyquinone for diethylene glycol as the starting material. m.p. 250–251° C.

EXAMPLE 44

Preparation of (I) 2-amino-5-(4-chlorophenylethynyl)-4-(4-hydroxyphenylthio)pyrimidine, and (II) 5-(4-chlorophenylethynyl)-2-formamido-4-(4-hydroxyphenylthio)pyrimidine 0.45 g of 4-mercaptophenol and 0.86 g of a 60% suspension of sodium hydride in mineral oil were stirred in 200 ml of tetrahydrofuran (dried over sieves) for 45 minutes then 2.17 g of 4-chloro-5-(4-chlorophenylethynyl)-2-formamidopyrimidine was added and the mixture was stirred at 25° C. under nitrogen for 5.5 hours. The reaction mixture was then filtered and the filtrate evaporated under reduced pressure at 50° C. The resulting residue was stirred with 300 ml of ethyl acetate and 250 ml of water for 45 minutes. The organic phase was washed with 250 ml of water and then 100 ml of brine. After drying over stirred sodium sulfate for 6.5 hrs. the cloudy suspension was filtered and the filtrate was combined with 11 g of silica gel 60 (230–400 mesh) and evaporated under reduced pressure at 50° C. The dried solids were applied to a column of silica gel 60 (2.5×6 cm). The final height of the column was 12 cm. After eluting the column with increasing concentrations of ethyl acetate in methylene chloride, the fractions were allowed to stand at 25° C. for 48 hours. Precipitates formed in two groups of fractions. Each was collected separately by filtration and washed with methylene chloride. The white solid from the earlier fractions was dried in vacuo at 105° C., m.p. 266–267° C. (0.13 g). The elemental analysis was consistent with the structure 5-(4-chlorophenylethynyl)-2-formamido-4-(4-hydroxyphenylthio)pyrimidine. The light yellow solid obtained from the later fractions was dried in vacuo at 105° C., m.p. 261–262° C. (0.18 g). The elemental analysis was consistent with the structure 2-amino-5-(4-chlorophenylethynyl)-4-(4-hydroxyphenylthio)pyrimidine.

Compounds (I) and (II) of Example 44 are subject to ex vivo or in vivo oxidation at the 4-position to produce the corresponding sulfoxide and/or sulfone derivatives, and such derivatives compounds are included within the scope of the present invention.

Assay for Activity

The compounds of the present invention were assayed for neurotrophic activity as follows:

A. Screen for NGF-Like Activity:

Cultured PC12 cells (rat adrenal pheochromocytoma from ATCC) have receptors for NGF. Responses include promotion of neurite outgrowth and elevation of choline acetyltransferase (ChAT) (L. A. Greene and A. S. Tischler, Cell Neurobiol., 3, 373 (1982)).

The following assay is modified from that described in H L White and P W Scates, Neurochem. Res., 16, 63 (1991). PC12 cells were cultured at 37° C. in RPMI supplemented with HEPES buffer, pH7.5 (to 10 mM), fetal bovine serum, horse serum, glutamine, penicillin, streptomycin and non-essential amino acids. Cultures were split 1:3 every 3 to 4 days. Exponentially dividing cells were plated into fresh medium on collagen-coated 12-well plastic dishes ($10^5$ cells/well). After allowing one day for cell attachment, the medium was replaced with low serum medium, with or without test compounds with each condition in triplicate. The medium may contain up to 0.2% ethanol, which was used as a solvent for most compounds tested. Cells were examined for morphological changes using an Olympus IMT-2 inverted research microscope. After 3 days incubation with test compounds, medium was removed and replaced with 0.2 ml of lysis and ChAT assay mixture. The plates were incubated at 37° C. for 2 hours and then placed into a freezer at −20° C.

Compounds are judged NGF-like in this primary screen if they (1) increase the activity of ChAT, (2) enhance NGF-stimulated neurite outgrowth or (3) potentiate or appear additive with the action of NGF itself.

B. Choline Acetyltransferase (ChAT) Assays:

The assay mixture contained 100 mM phosphate, pH7.4, 0.1% NP40, 150 mM NaCl, 1.5 mM choline, 10 mM EDTA, 0.1 mM eserine, 0.1 mM acetyl-coenzyme A and about 0.5 uCi (40–70 Ci/mol) [14C]acetyl-coenzyme A in each ml of mixture. Thawed and lysed cell reaction mixtures were diluted to 1 ml with water and transferred to 7 ml scintillation vials containing 5 ml of extraction/scintillation fluid solution (50 mg triphenyl borate, 50 mg PPO, 20 mg POPOP per 100 ml of 20% acetonitrile/80% toluene) and vortexed for 10 seconds. After all 20 diluted well contents were transferred and mixed, all the vials were vortexed again for 30 seconds, rotated for about 2 hours, and then vortexed once more. The vials were centrifuged at 3000 rpm (rmax.=16 cm) for 15 minutes and then counted in a Beckman LS6500 scintillation counter. Background counts from reaction mixtures with extracts from non-stimulated cells (no NGF and no test compound) were subtracted from reaction product counts before comparisons of ChAT activities were made.

The following data were obtained for representative compounds of the present invention which (1) increased the activity of choline acetyltransferase ChAT), (2) enhanced NGF-stimulated neurite outgrowth and/or (3) potentiated or appeared additive with the action of NGF itself. The concentration at which the test compound doubled the ChAT activity over the activity with NGF alone (no test compound) was recorded as the $EC_{2x}$ value. Among the more active compounds of the present invention are the following:

| Compound of | EC$_{2x}$ (uM) |
| --- | --- |
| Example 4 | 0.2 |
| Example 9 | 0.1 |
| Example 12 | 0.2 |
| Example 13 | 0.3 |
| Example 14 | 0.5 |
| Example 23 | 0.3 |
| Example 26 | 0.2 |

The invention claimed is:

1. A compound of Formula I:

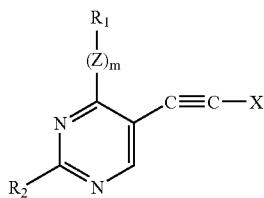

Formula I wherein

Z is O, NH or S, and m is 0 or 1;

R$_1$ is (C2–6alkyl)$_a$(C3–10cycloalkyl, C2–9heterocycloalkyl, C5–10aryl, or C4–9heteroaryl)$_b$(C1–6alkyl)$_c$, wherein a, b and c are independently 0 or 1, provided that at least one of a, b and c is 1 and if b is 0, then c is also 0, further provided that, when a is 1, the C2–6alkyl group is the point of attatchment and, when a is 0, the cyclic moity of R$_1$ is the point of attatchment, and wherein the hetrogroups include from 1 to 4 hetroatoms selected from the group consisting of N, O and S, and the C and N atoms of the R$_1$ may optionally be substituted woth one or more substituents selected from the group consisting of:

OH;
halogen:
thio;
oxo;
thioxo;
carboxy;
carboxamide;
C1–7alkylcarbonyl;
C1–7alkylcarbonyloxy
C1–7alkylthiocarbonyl;
C1–8alkyloxy;
hydroxyC2–8alkyloxy;
di-C1–8alkylphosphate ester
C1–8alkylthio;
hydroxyC2–8alkylthio;
C1–8alkylsulfinyl;
C1–8alkylsulfonyl;
C1–5alkyloxyC1–5alkyl;
C1–5alkylthioC1–5alkyl;
C1–5alkylsulfinylC1–5alkyl; and
C1–5alkylsulfonylC1–5alkyl;

R$_2$ is selected from the group consisting of H, NH$_2$ and NH—CO—R$_3$, where R$_3$ is H or C1–12 alkyl; and X is C6–10aryl optionally substituted with one or more substituents (y) selected from the group consisting of:

OH;
NO$_2$
NH$_2$
NH—CO—R$_4$ where R$_4$ is H, C1–12alkyl, aryl or (C1–6alkyl)aryl
halogen;
C1–6alkyl;
hydroxyC1–6alkyl;
oxoC2–7alkyl;
C2–7alkenyl;
C2–7alkynyl;
C1–6alkoxy;
CF$_3$;
CF$_3$C1–6alkyl;
OCF$_3$; and
CF$_3$C1–6alkoxy;

or a pharmaceutically acceptable salt thereof.

2. A compound of claim 1, wherein m is 1 and X is phenyl.

3. A compound of claim 1, wherein m is 1, X is phenyl and R$_1$ is C2–6alkyl, C3–10cycloalkyl, C6–10aryl, or C6–10arylC2–6alkyl.

4. A compound of claim 1, wherein m is 1 and X is phenyl and R$_1$ is ethyl, cyclohexyl, phenyl or phenylethyl.

5. A compound of claim 1, wherein m is 0, X is phenyl and R$_1$ is piperidino or piperazino.

6. A compound of claim 1 selected from:

2-Amino-5-(4-chlorophenylethynyl)-4-(4-acetylpiperazino)pyrimidine,
4-(trans-4-Hydroxycyclohexylamino)-5-phenylethynylpyrimidine,
4-[2-(2-Hydroxyethoxy)ethylamino]-5-phenylethynylpyrimidine,
5-(4-Chlorophenylethynyl)-4-[2-(2-hydroxyethoxy)ethylamino]pyrimidine,
2-Amino-5-(4-chlorophenylethynyl)-4-[2-(2-hydroxyethoxy)ethylamino]pyrimidine,
4-(4-(2-Hydroxyethyl)piperazino)-5-phenylethynylpyrimidine,
2-Amino-4-(4-(2-hydroxyethyl)piperazino)-5-phenylethynylpyrimidine,
2-Amino-5-(4-chlorophenylethynyl)-4-(4-(2-hydroxyethyl)piperazino)pyrimidine,
4-(4-Hydroxypiperidino)-5-phenylethynylpyrimidine,
5-(4-Chlorophenylethynyl)-4-(4-hydroxypiperidino)pyrimidine,
2-Amino-4-(4-hydroxypiperidino)-5-phenylethynylpyrimidine,
2-Amino-5-(4-chlorophenylethynyl)-4-(4-hydroxypiperidino)pyrimidine,
4-(2-Hydroxyethylamino)-5-phenylethynylpyrimidine,
2-Amino-4-(2-hydroxyethylamino)-5-phenylethynylpyrimidine,
2-Amino-4-(4-hydroxyanilino)-5-phenylethynylpyrimidine,
2-Amino-4-(4-trans-hydroxycyclohexylamino)-5-(4-n-pentylphenylethynyl) pyrimidine,
2-Acetamido-4-(4-trans-acetoxycyclohexylamino)-5-(4-chlorophenylethynyl) pyrimidine,
2-Amino-5-(4-t-butylphenylethynyl)-4-(4-trans-hydroxycyclohexylamino) pyrimidine,
2-Amino-5-(4-chlorophenylethynyl)-4-(4-hydroxyphenylethylamino)pyrimidine,
2-Amino-4-(4-hydroxyanilino)-5-(4-methoxyphenylethynyl)pyrimidine,
2-Amino-5-(4-propylphenylethynyl)-4-(4-trans-hydroxycyclohexylamino) pyrimidine,
2-Amino-4-(4-hydroxy-2-methylanilino)-5-(4-chlorophenylethynyl)pyrimidine,
2-Amino-5-(4-chlorophenylethynyl)-4-(4-hydroxyanilino)pyrimidine, 2-Amino-5-(4-chlorophenylethynyl)-4-(4-oxocyclohexyloxy)pyrimidine,
2-amino-5-(4-chlorophenylethynyl)-4-[2-(2-hydroxyethoxy)ethoxy] pyrimidine,
2-amino-5-(4-chlorophenylethynyl)-4-(4-hydroxyphenoxy)pyrimidine,
2-amino-5-(4-chlorophenylethynyl)-4-(4-hydroxyphenylthio)pyrimidine,
5-(4-chlorophenylethynyl)-2-formamido-4-(4-hydroxyphenylthio)pyrimidine,
4-(4-Hydroxyanilino)-5-phenylethynylpyrimidine,
5-(4-Chlorophenylethynyl)-4-(4-hydroxyanilino)pyrimidine,
2-Amino-4-[2-(2-hydroxyethoxy)ethylamino]-5-(4-methylphenylethynyl)pyrimidine,
2-Amino-4-(trans-hydroxycyclohexylamino)-5-(4-methylphenylethynyl)pyrimidine,
5-(4-Chlorophenylethynyl)-2-formamido-4-(4-trans-hydroxycyclohexylamino) pyrimidine,
2-Amino-5-(3,4-dichlorophenylethynyl)-4-(4-trans-hydroxycyclohexylamino) pyrimidine,
2-Amino-5-(4-chlorophenylethynyl)-4-(4-oxocyclohexylamino)pyrimidine,
2-Amino-5-(2-chlorophenylethynyl)-4-(4-trans-hydroxycyclohexylamino) pyrimidine,
2-Amino-5-(4-bromophenylethynyl)-4-(4-trans-hydroxycyclohexylamino) pyrimidine,
2-Amino-5-(4-chlorophenylethynyl)-4-(4-trans-hydroxycyclohexylamino) pyrimidine-O-dimethylphosphate ester,
2-Amino-5-(4-chlorophenylethynyl)-4-(3,4-dimethoxyanilino)pyrimidine, and
5-(4-Acetamidophenylethynyl)-2-amino-4-(4-trans-hydroxycyclohexylamino) pyrimidine.

7. A compound of claim 1 selected from:
5-(4-Chlorophenylethynyl)-4-(trans-4-hydroxycyclohexylamino)pyrimidine,
2-Amino-5-(4-chlorophenylethynyl)-4-(4-hydroxyanilino)pyrimidine,
2-Amino-4-(trans-4-hydroxycyclohexylamino)-5-phenylethynylpyrimidine,
2-Amino-5-(4-chlorophenylethynyl)-4-(trans-4-hydroxycyclohexylamino) pyrimidine,
2-Amino-5-(4-chlorophenylethynyl)-4-(cis-4-hydroxycyclohexylamino)pyrimidine,
2-Amino-4-[2-(2-hydroxyethoxy)ethylamino]-5-phenylethynylpyrimidine,
2-Amino-5-(4-chlorophenylethynyl)-4-(2-hydroxyethylamino)pyrimidine, and
2-Amino-5-(4-ethylphenylethynyl)-4-(trans-hydroxycyclohexylamino)pyrimidine.

8. A compound of claim 1 according to Formula IA:

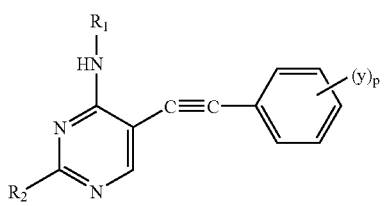

Formula IA wherein p is 0, 1 or 2, and each y (which may be the same or different), $R_1$ and $R_2$ are as defined in claim 1, or a pharmaceutically acceptable salt thereof.

9. A compound of claim 8, wherein $R_1$ is C2–6alkyl, C3–10cycloalkyl, C6–10aryl, or C6–10arylC2–6alkyl.

10. A compound of claim 8, wherein $R_1$ is hydroxycyclohexyl, hydroxyphenyl, hydroxyphenylethyl, hydroxyethyl or hydroxyethoxyethyl.

11. A compound of claim 1 according to Formula IB

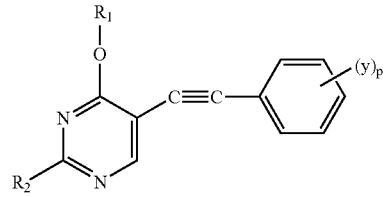

Formula IB wherein p is 0, 1 or 2, and each y (which may be the same or different), $R_1$ and $R_2$ are as defined in claim 1, or a pharmaceutically acceptable salt thereof.

12. A compound of claim 11, wherein $R_1$ is C2–6alkyl, C3–10cycloalkyl, C6–10aryl, or C6–10arylC2–6alkyl.

13. A compound of claim 11, wherein $R_1$ is hydroxycyclohexyl, hydroxyphenyl, hydroxyphenylethyl, hydroxyethyl or hydroxyethoxyethyl.

14. A compound of claim 1 according to Formula IC

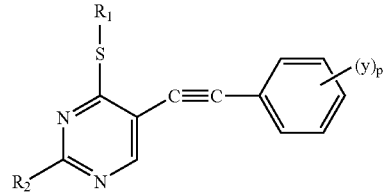

Formula IC wherein p is 0, 1 or 2, and each y (which may be the same or different), $R_1$ and $R_2$ are as defined in claim 1, or a pharmaceutically acceptable salt thereof.

15. A compound of claim 14, wherein $R_1$ is C2–6alkyl, C3–10cycloalkyl, C6–10aryl, or C6–10arylC2–6alkyl.

16. A compound of claim 14, wherein $R_1$ is hydroxycyclohexyl, hydroxyphenyl, or hydroxyethoxyethyl.

17. A pharmaceutical composition, comprising a compound of claim 1 and a pharmaceutically acceptable carrier therefor.

18. A method of treating a mammal having a neurodegenerative or neurological disorder of the central or peripheral nervous system selected from the group consisting of Alzheimer's disease, peripheral neuropathy, senile dementia, seizure disorders, Huntington's disease, and Parkinson's disease, which comprises administering to said mammal a therapeutically effective amount of a compound of claim 1.

19. A pharmaceutical composition, comprising a compound of claim 6 and a pharmaceutically acceptable carrier therefor.

20. A pharmaceutical composition, comprising a compound of claim 7 and a pharmaceutically acceptable carrier therefor.

21. A method of treating a mammal having a neurodegenerative or neurological disorder of the central or peripheral nervous system selected from the group consisting of Alzheimer's disease, peripheral neuropathy, senile dementia, seizure disorders, Huntington's disease, and Parkinson's disease, which comprises administering to said mammal a therapeutically effective amount of a compound of claim 6.

22. A method of treating a mammal having a neurodegenerative or neurological disorder of the central or peripheral nervous system selected from the group consisting of Alzheimer's disease, peripheral neuropathy, senile dementia, seizure disorders, Huntington's disease, and Parkinson's disease, which comprises administering to said mammal a therapeutically effective amount of a compound of claim 7.

23. A method according to claim 18, wherein the disorder is Alzheimer's disease.

24. A method according to claim 21, wherein the disorder is Alzheimer's disease.

25. A method according to claim 22, wherein the disorder is Alzheimer's disease.

26. A method according to claim 18, wherein the disorder is peripheral neuropathy.

27. A method according to claim 21, wherein the disorder is peripheral neuropathy.

28. A method according to claim 22, wherein the disorder is peripheral neuropathy.

29. A method according to claim 18, wherein the disorder is senile dementia.

30. A method according to claim 21, wherein the disorder is senile dementia.

31. A method according to claim 22, wherein the disorder is senile dementia.

32. A method according to claim 18, wherein the disorder is a seizure disorder.

33. A method according to claim 21, wherein the disorder is a seizure disorder.

34. A method according to claim 22, wherein the disorder is a seizure disorder.

35. A method according to claim 18, wherein the disorder is Huntington's disease.

36. A method according to claim 21, wherein the disorder is Huntington's disease.

37. A method according to claim 22, wherein the disorder is Huntington's disease.

38. A method according to claim 18, wherein the disorder is Parkinson's disease.

39. A method according to claim 21, wherein the disorder is Parkinson's disease.

40. A method according to claim 22, wherein the disorder is Parkinson's disease.

* * * * *

UNITED STATES PATENT AND TRADEMARK OFFICE
CERTIFICATE OF CORRECTION

PATENT NO. : 7,205,297 B2
APPLICATION NO. : 10/333447
DATED : April 17, 2007
INVENTOR(S) : Beauchamp et al.

It is certified that error appears in the above-identified patent and that said Letters Patent is hereby corrected as shown below:

On the Title Page,

<u>Item (87) PCT Pub. Date</u>: "Jan. 3, 2002" should read --Jan. 31, 2002--

<u>Column 19,</u>

<u>Line 5:</u> "5 A mixture" should read --A mixture--

<u>Column 25,</u>

<u>Line 29:</u> "C5-10aryl" should read --C6-10aryl--

<u>Line 34:</u> "moity" should read --moiety--

<u>Line 36:</u> "fron" should read --from--

<u>Line 38:</u> "woth" should read --with--

Signed and Sealed this

Fourth Day of March, 2008

JON W. DUDAS
*Director of the United States Patent and Trademark Office*